(12) United States Patent
Roux et al.

(10) Patent No.: US 7,763,709 B2
(45) Date of Patent: Jul. 27, 2010

(54) NUCLEIC ACID AND ALLERGENIC POLYPEPTIDES ENCODED THEREBY IN CASHEW NUTS

(75) Inventors: Kenneth Roux, Tallahassee, FL (US); Suzanne Teuber, Davis, CA (US); Shridhar K. Sathe, Tallahassee, FL (US); Jason Robotham, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 2 days.

(21) Appl. No.: 11/906,801

(22) Filed: Oct. 4, 2007

(65) Prior Publication Data
US 2009/0092959 A1  Apr. 9, 2009

Related U.S. Application Data

(62) Division of application No. 10/529,602, filed as application No. PCT/US2003/034960 on Apr. 11, 2003, now Pat. No. 7,537,914.

(60) Provisional application No. 60/423,556, filed on Nov. 4, 2002.

(51) Int. Cl.
 *A61K 38/10* (2006.01)
 *A61K 39/35* (2006.01)
 *C07K 14/415* (2006.01)
 *C07K 16/42* (2006.01)

(52) U.S. Cl. ............ 530/326; 530/324; 530/370; 530/391.1; 530/391.3; 424/185.1; 424/275.1; 435/7.1; 435/810

(58) Field of Classification Search ............ None
See application file for complete search history.

(56) References Cited

U.S. PATENT DOCUMENTS

| | | | | |
|---|---|---|---|---|
| 6,884,877 | B2 * | 4/2005 | Roux et al. | 536/23.1 |
| 7,381,534 | B1 * | 6/2008 | Roux et al. | 435/7.1 |
| 7,537,914 | B1 * | 5/2009 | Roux et al. | 435/69.1 |
| 7,538,203 | B1 * | 5/2009 | Roux et al. | 536/23.1 |
| 2003/0124060 | A1 * | 7/2003 | Roux et al. | 424/9.81 |

FOREIGN PATENT DOCUMENTS

WO  WO99/45961 A1 * 9/1999
WO  WO01/75067 A2 * 10/2001

OTHER PUBLICATIONS

Chica et al, Curr Opin Biotechnol 16(4):378-84, Aug. 2005.*
Stanley et al, Arch Biochem Biophys 342(2): 244-53, Jun. 1997.*

* cited by examiner

*Primary Examiner*—Phuong Huynh
(74) *Attorney, Agent, or Firm*—Allen, Dyer, Doppelt, Milbrath & Gilchrist, P.A.

(57) ABSTRACT

The invention describes an isolated nucleic acid sequence comprising the nucleotide sequence of SEQ ID NO: 1 or a degenerate variant of SEQ ID NO:1. The nucleic acid sequence encodes an Ig-E binding immunogenic polypeptide the amino acid sequence of which comprises at least one sequence selected from SEQ ID NOS:4-25. The invention additionally provides an in vitro diagnostic test for detecting anti-cashew IgE in a patient. The test comprises reacting the patient's serum with a purified polypeptide the amino acid sequence of which comprises at least one sequence selected from SEQ ID NOS:3-25; separating the polypeptide from unreacted patient serum; reacting the polypeptide with a labeled human IgE-reactive agent after separating from unreacted patient serum; separating the polypeptide from unreacted labeled human IgE-reactive agent; and detecting labeled human IgE-reactive agent bound to the polypeptide after separating from unreacted agent to thereby indicate presence in the patient's serum of anti-cashew IgE.

4 Claims, 7 Drawing Sheets

FIG. 1 A1.

```
1    CTTTCTGTTTGCTTTTTAATTCTCTTTCATGGTTGCCTAGCTTCTCGCCAGGAATGGCAACAACAAGATGAGTGCCAAA
81   TCGATAGGCTGGATGCCCTTGAACCCGATAACCGAGTTGAGTATGAAGCCGGTACGGTGGAAGCCTGGGATCCTAACCAT
161  GAGCAATTCCGATGCGCTGGTGTTGCCTTGGTTAGGCATACCATCCAACCTAATGGCCTTCTCTTGCCTCAATATTCTAA
241  TGCTCCTCAACTTATTTACGTTGTCCAGGGTGAGGGTATGACAGGAATATCATATCCAGGATGCCCAGAAACTTACCAAG
321  CGCCCCAACAGGGACGACAACAGGGACAGAGTGGTAGGTTCCAGGACCGGCATCAAAAGATTCGACGCTTCCGTCGAGGC
401  GATATCATCGCAATCCCCGCCGGAGTAGCACACTGGTGCTACAACGAGGGCAATTCCCCGGTCGTCACTGTTACTCTTCT
481  AGACGTCTCAAACAGTCAAAATCAGCTTGATAGGACCCCACGAAAATTCCATCTGGCTGGTAACCCAAAAGATGTGTTCC
561  AGCAGCAGCAACAACACCAATCTCGCGGGCGTAACCTTTTTTCTGGCTTCGATACAGAGTTATTGGCTGAGGCTTTCCAA
641  GTGGACGAACGTCTCATAAAGCAGCTCAAAAGCGAGGACAACAGGGGTGGCATTGTTAAGGTGAAGGATGACGAACTTCG
721  GGTGATCCGCCCATCAAGGAGTCAGAGCGAGCGTGGAAGTGAGAGTGAAGAGGAAAGTGAGGATGAAAAACGCCGATGGG
801  GACAGCGTGACAATGGGATTGAAGAGACCATTTGCACTATGAGACTCAAAGAGAATATCAATGATCCTGCTCGCGCTGAC
881  ATTTACACCCCAGAAGTCGGTCGTCTTACCACACTCAACAGCCTCAACCTCCCAATCCTCAAATGGCTTCAACTCAGTGT
961  TGAAAAGGGTGTGCTATACAAAAATGCTCTAGTGCTGCCACACTGGAACCTCAACTCGCACAGCATAATATACGGGTGCA
1041 AGGGTAAAGGCCAGGTTCAAGTAGTAGACAACTTCGGCAACAGAGTGTTCGACGGCGAAGTCCGCGAGGGACAGATGTTG
1121 GTGGTGCCACAAAACTTTGCAGTAGTGAAACGTGCAAGAGAGGAAAGATTCGAATGGATTTCTTTCAAGACCAATGATCG
1201 GGCCATGACGAGTCCTCTCGCTGGACGCACCTCGGTGCTTGGTGGCATGCCAGAGGAAGTGTTAGCCAATGCGTTCCAGA
1281 TCTCAAGAGAAGATGCTAGGAAGATCAAGTTCAACAATCAGCAGACAACTTTGACAAGTGGAGAGTCAAGCCACCACATGA
1361 GGGATGATGCTTAA
```

FIG. 1 A2

1 ATTTTAAGTAATAATTTGAGCTGAGCTAGTGGTGATTTAAAGCCGAATGCATGTGGTGTACGTACTATGTTTTGTTTTGCT
81 TTGTAAGGGGGATAGGTAATGAATAATAAAGGAGAGCTTGGATAGTCTGCTGTGAGAGGGAGAGAAGCAGGAGAGC
161 AGAGAGCAGAGAGCTTGTATGTAGTTAAGTTAATATTACTACTACTACTACGATGTGAATGAACTCTTGATGAGTTC
241 TGTCCAATAAAAACTACTTTCCTACTCAAAAAAAAAAAAAAAAAAAAA

FIG. 1B

```
1   LSVCFLILFH GCLASRQEWQ QQDECQIDRL DALEPDNRVE YEAGTVEAWD PNHEQFRCAG
61  VALVRHTIQP NGLLLPQYSN APQLIYVVQG EGMTGISYPG CPETYQAPQQ GRQQGQSGRF
121 QDRHQKIRRF RRGDIIAIPA GVAHWCYNEG NSPVVTVTLL DVSNSQNQLD RTPRKFHLAG
181 NPKDVFQQQQ QHQSRGRNLF SGFDTELLAE AFQVDERLIK QLKSEDNRGG IVKVKDDELR
241 VIRPSRSQSE RGSESEEESE DEKRRWGQRD NGIEETICTM RLKENINDPA RADIYTPEVG
301 RLTTLNSLNL PILKWLQLSV EKGVLYKNAL VLPHWNLNSH SIIYGCKGKG QVQVVDNFGN
361 RVFDGEVREG QMLVVPQNFA VVKRAREERF EWISFKTNDR AMTSPLAGRT SVLGGMPEEV
421 LANAFQISRE DARKIKFNNQ QTTLTSGESS HHMRDDA 457
```

FIG. 1 C.

```
            Cav Ms Car Cp        Cp
             5  14  4  11         5
 14         A|S|RQ|E|WQQQ|D  23

Car         Ah3,4-Ms Ahy  Ahy  Cav
             17          12-4     6    9    7
105         Y|QAPQQGR|QQG|QSG|RF|Q  121

Mg      Cav    Rc Qr Si      V  Ah3,4 Cp-Rc-Ahy
     5       21    7  8  6       7   41    9-10-7
180 G|NPKD|VFQ|Q|Q|QQHQ|SR|GR|N  198

Ah3-4              Qr
     3-4                7
225 E|DNRGGIVKVK|D  236

Ah3          Vs              Ah3,4 Cav-Vs
     4   Ms      19              Cp    4   8-7
245 SRS|QSERGSES|EEESEDEKRRWGQ|RD|N  271
         Ahy                      Si
```

FIG. 1 D.

| | |
|---|---|
| cDNA segment | 30 LDALEPDNR 38 |
| Tryptic fragment, | LDALEPDNK |
| | |
| cDNA segment | 72 GLLLPQYSNAPQLIYVVQG 91 |
| Tryptic fragment, | GLLVPSYNN-PELVYVVQG |
| Tryptic fragment, | GLLVPSYNN-PELVYVVQ |
| | |
| cDNA segment | 272 GIEETICTMR 281 |
| N-terminal fragment, | GLEETICTMT |
| | M |

FIG. 3

Ana o 2: 1 ▓▓▓▓▓▓▓▓▓▓▓▓▓▓▓▓▓▓▓▓▓▓▓▓▓▓▓▓▓▓▓▓▓▓▓▓NRVEYEAGTVEAWDPNHEQFRCAGVALVRHTIQP 70
Ara h 3: 2 ---------------F½½QP½½½A·FQ·½·QR····½·S·G·Y½·T·½··½½½E······S·LV½½R 57
G1 glyc: 7 -½···½FSGC·F·F·S½·QP··½····Q½·½··½····½·S·G·L½·T·½··½½P·½······S·C·½NR 76
G2 glyc: 6 ▓▓·▓S·F·-L·½½-A··½····Q½·½··½····½·S·G·F½·T·½··½½P·½······S·C·½NR 73

Ana o 2: 71 NGLLLPQYSNAPQLIYVV▓▓▓▓▓▓▓▓▓▓▓▓▓▓▓▓▓▓▓▓▓▓▓▓▓▓▓▓▓
▓▓▓▓▓▓▓▓▓▓▓▓▓▓▓▓▓▓▓▓▓▓▓▓▓ 136
Ara h 3: 58 ·A·RR·F·····E·½½Q·R·YF·½I½·····RH·½E·HT····½/½D··Q½Q·½·S····½H·DE····½·· 136
G1 glyc: 77 ·A·RR·S·½·G··E··½Q···½·½F·½I·····S·½½E····P½··½···S·P······YN·E·½·· 142
G2 glyc: 74 ·A·RR·S·½·G··E·½·Q·N·½F·½I½·····S···E··-½S½-·½·½·Q·P······½H···E·½·· 139

Ana o 2: 137 ▓▓▓▓▓▓▓▓▓▓▓▓▓▓▓▓▓▓▓▓SPVVTVTLLDVSNSQ▓▓Q▓▓▓▓▓▓▓▓▓▓▓▓▓▓▓▓D▓▓
▓▓▓▓▓▓▓▓▓▓▓▓▓▓▓▓ 198
Ara h 3: 137 ·½·T···F·L··½H½½D··A·½·T·T½··½D····½F··½·½···T½QE·/Y···SR···/·G··241
G1 glyc: 143 ·½·T···W·M··NE½½····A·½½½·T½½L½·····½M··½·½····Q½QE·/½H···½E½½·E-·G½· 219
G2 glyc: 140 ·½·T···W·M··NE½½····A·½½½·T½½L½·····½M··½·½····Q½QE·/···½½½E-·S· 215

Ana o 2: 199 LFSGFDTELLAEAFQVDE▓▓▓▓▓▓▓▓▓▓▓▓▓▓▓▓▓▓▓▓▓▓V▓V▓DDE▓▓V▓·▓▓▓▓
▓▓▓▓▓▓▓▓E 256
Ara h 3: 242 ·½····TP·F·E½······½·Q½½½N·½G·/½EE·A··T·½GG-··½½S·D-·K/½E·E·│·D··306
G1 glyc: 220 ▓L···TL·F·EH··S··½½-½A·N·½G·/½½½½·A··T·GGLSV··½KP·½-DE··Q½·PQ·E··280
G2 glyc: 216 ½L···AP·F·K···G·½M½-½½½N·½/-½½S·A··T·GG····TA·½/½P--Q·EDD½D··276

β Acidic Subunit ⁻ Basic Subunit à

Ana o 2: 257 ▓▓▓▓▓▓▓▓▓▓▓▓▓▓▓▓▓▓▓▓▓▓GIEETICTMRLKENINDPARADIYTPEVGRLTTLNS 307
Ara h 3: 307 Y·Y-½½·D-··R·½/·G-·│·····ASA·½·GRNRSP··N·½A·LSK·A·D·· 360
G1 glyc: 281 E-·····P½·CKG-½·/··│·½·······½H·GQT½SP··N·½A·S½··AT··346
G2 glyc: 277 Q/·T½·T·½SK½-SR-···½········½½·GQN½SP··N·½A·S½··AT··336

Ana o 2: 308
LNLP▓▓▓▓▓▓▓▓▓▓▓▓▓▓▓▓▓▓N▓▓▓▓▓▓▓▓▓▓▓▓▓▓▓▓▓▓▓▓▓▓▓▓▓▓▓VQVVDNFGNRVFDGEVREGQM
372
Ara h 3: 361 ··L·½··G··A·Y·N··½··F½A·½·T·½·····RL½·½AH·····½N····½·E·½½···H½ 426
G1 glyc: 347 ·½F·A·S···½··A·F·S·R····½F½·½···½½·····ALN·½AL½····½CN·E······½½···½½ 406
G2 glyc: 337 ▓½F·A·WL·½·A·½YS·R····½F½··½T··½½·····ALN·½AL·····½CN·E······½½···G·½ 401

Ana o 2: 373
LVVP▓▓▓▓▓▓▓▓▓▓▓▓▓▓▓▓▓▓▓▓▓▓▓▓▓▓▓▓RAMTSPLAGRTSVLGGM▓▓▓▓▓▓▓▓▓▓▓▓▓▓▓▓▓▓▓▓▓▓▓▓▓
▓QQT 442
Ara h 3: 427 ········AG½½½S·N··½½½·····½S·PSI½N···EN··½DN½·····½··½½½G½Q··Q··½½·N··  493
G1 glyc: 407 ·½······V·AA·½½S½N··½½·······TP·IGT···AN·½·NA½····½Q½T·N½KS½Q··½··N··  478
G2 glyc: 402 ·½······AA½½½S½N··½½·······PSIGN··AN·½·NA½····½Q½T·N½KS½Q···½N·PF½· 470

SEQUENCE LISTING

```
<160> NUMBER OF SEQ ID NOS: 27

<210> SEQ ID NO 1
<211> LENGTH: 1374
<212> TYPE: DNA
<213> ORGANISM: Anacardium occidentale

<400> SEQUENCE: 1
ctttctgttt gctttttaat tctctttcat ggttgcctag cttctcgcca ggaatggcaa      60
caacaagatg agtgccaaat cgataggctg gatgcccttg aacccgataa ccgagttgag     120
tatgaagccg gtacggtgga agcctgggat cctaaccatg agcaattccg atgcgctggt     180
gttgccttgg ttaggcatac catccaacct aatggccttc tcttgcctca atattctaat     240
gctcctcaac ttatttacgt tgtccagggt gagggtatga caggaatatc atatccagga     300
tgcccagaaa cttaccaagc gccccaacag ggacgacaac agggacagag tggtaggttc     360
caggaccggc atcaaaagat tcgacgcttc cgtcgaggcg atatcatcgc aatccccgcc     420
ggagtagcac actggtgcta caacgagggc aattccccgg tcgtcactgt tactcttcta     480
gacgtctcaa acagtcaaaa tcagcttgat aggacccac gaaaattcca tctggctggt     540
aacccaaaag atgtgttcca gcagcagcaa caacaccaat ctcgcgggcg taacctttt     600 tctggcttcg atacagagtt attggctgag gctttccaag tggacgaacg tctcataaag     660
cagctcaaaa gcgaggacaa caggggtggc attgttaagg tgaaggatga cgaacttcgg     720
gtgatccgcc catcaaggag tcagagcgag cgtggaagtg agagtgaaga ggaaagtgag     780
gatgaaaaac gccgatgggg acagcgtgac aatgggattg aagagaccat ttgcactatg     840
agactcaaag agaatatcaa tgatcctgct cgcgctgaca tttacacccc agaagtcggt     900
cgtcttacca cactcaacag cctcaacctc ccaatcctca aatggcttca actcagtgtt     960
gaaaagggtg tgctatacaa aaatgctcta gtgctgccac actggaacct caactcgcac    1020
agcataatat acgggtgcaa gggtaaaggc caggttcaag tagtagacaa cttcggcaac    1080
agagtgttcg acggcgaagt ccgcgaggga cagatgttgg tggtgccaca aaactttgca    1140
gtagtgaaac gtgcaagaga ggaaagattc gaatggattt ctttcaagac caatgatcgg    1200
gccatgacga gtcctctcgc tggacgcacc tcggtgcttg gtggcatgcc agaggaagtg    1260
```

-continued

```
ttagccaatg cgttccagat ctcaagagaa gatgctagga agatcaagtt caacaatcag   1320
cagacaactt tgacaagtgg agagtcaagc caccacatga gggatgatgc ttaa         1374
```

<210> SEQ ID NO 2
<211> LENGTH: 296
<212> TYPE: DNA
<213> ORGANISM: Anacardium occidentale

<400> SEQUENCE: 2

```
attttaagta atttgagctg agctagtggt gatttaaagc cgaatgcatg tggtgtacgt    60
actatgtttt ttgttttgct ttgtaagggg gataggtaat gaataataaa ggagagcttg   120
gatagtctct gctgtgagag gggagaagaa agcagggagc agagagcaga gagcttgtat   180
gtagttaagt taatattact actactacta ctacgatgtg aatgaactct tgatgagttc   240
tgtccaataa aaaactactt ttcctactca aaaaaaaaaa aaaaaaaaaa aaaaaa       296
```

<210> SEQ ID NO 3
<211> LENGTH: 457
<212> TYPE: PRT
<213> ORGANISM: Anacardium occidentale

<400> SEQUENCE: 3

```
Leu Ser Val Cys Phe Leu Ile Leu Phe His Gly Cys Leu Ala Ser Arg
1               5                  10                  15

Gln Glu Trp Gln Gln Gln Asp Glu Cys Gln Ile Asp Arg Leu Asp Ala
            20                  25                  30

Leu Glu Pro Asp Asn Arg Val Glu Tyr Glu Ala Gly Thr Val Glu Ala
        35                  40                  45

Trp Asp Pro Asn His Glu Gln Phe Arg Cys Ala Gly Val Ala Leu Val
    50                  55                  60

Arg His Thr Ile Gln Pro Asn Gly Leu Leu Leu Pro Gln Tyr Ser Asn
65                  70                  75                  80

Ala Pro Gln Leu Ile Tyr Val Val Gln Gly Glu Gly Met Thr Gly Ile
                85                  90                  95

Ser Tyr Pro Gly Cys Pro Glu Thr Tyr Gln Ala Pro Gln Gln Gly Arg
            100                 105                 110

Gln Gln Gly Gln Ser Gly Arg Phe Gln Asp Arg His Gln Lys Ile Arg
        115                 120                 125

Arg Phe Arg Arg Gly Asp Ile Ile Ala Ile Pro Ala Gly Val Ala His
    130                 135                 140

Trp Cys Tyr Asn Glu Gly Asn Ser Pro Val Val Thr Val Thr Leu Leu
145                 150                 155                 160

Asp Val Ser Asn Ser Gln Asn Gln Leu Asp Arg Thr Pro Arg Lys Phe
                165                 170                 175

His Leu Ala Gly Asn Pro Lys Asp Val Phe Gln Gln Gln Gln His
            180                 185                 190

Gln Ser Arg Gly Arg Asn Leu Phe Ser Gly Phe Asp Thr Glu Leu Leu
        195                 200                 205

Ala Glu Ala Phe Gln Val Asp Glu Arg Leu Ile Lys Gln Leu Lys Ser
    210                 215                 220

Glu Asp Asn Arg Gly Gly Ile Val Lys Val Lys Asp Glu Leu Arg
225                 230                 235                 240

Val Ile Arg Pro Ser Arg Ser Gln Ser Glu Arg Gly Ser Glu Ser Glu
                245                 250                 255
```

-continued

```
Glu Glu Ser Glu Asp Glu Lys Arg Arg Trp Gly Gln Arg Asp Asn Gly
            260                 265                 270

Ile Glu Glu Thr Ile Cys Thr Met Arg Leu Lys Glu Asn Ile Asn Asp
        275                 280                 285

Pro Ala Arg Ala Asp Ile Tyr Thr Pro Glu Val Gly Arg Leu Thr Thr
    290                 295                 300

Leu Asn Ser Leu Asn Leu Pro Ile Leu Lys Trp Leu Gln Leu Ser Val
305                 310                 315                 320

Glu Lys Gly Val Leu Tyr Lys Asn Ala Leu Val Leu Pro His Trp Asn
                325                 330                 335

Leu Asn Ser His Ser Ile Ile Tyr Gly Cys Lys Gly Lys Gly Gln Val
            340                 345                 350

Gln Val Val Asp Asn Phe Gly Asn Arg Val Phe Asp Gly Glu Val Arg
        355                 360                 365

Glu Gly Gln Met Leu Val Val Pro Gln Asn Phe Ala Val Val Lys Arg
    370                 375                 380

Ala Arg Glu Glu Arg Phe Glu Trp Ile Ser Phe Lys Thr Asn Asp Arg
385                 390                 395                 400

Ala Met Thr Ser Pro Leu Ala Gly Arg Thr Ser Val Leu Gly Gly Met
                405                 410                 415

Pro Glu Glu Val Leu Ala Asn Ala Phe Gln Ile Ser Arg Glu Asp Ala
            420                 425                 430

Arg Lys Ile Lys Phe Asn Asn Gln Gln Thr Thr Leu Thr Ser Gly Glu
        435                 440                 445

Ser Ser His His Met Arg Asp Asp Ala
    450                 455

<210> SEQ ID NO 4
<211> LENGTH: 15
<212> TYPE: PRT
<213> ORGANISM: Anacardium occidentale

<400> SEQUENCE: 4

Leu Ser Val Cys Phe Leu Ile Leu Phe His Gly Cys Leu Ala Ser
1               5                   10                  15

<210> SEQ ID NO 5
<211> LENGTH: 15
<212> TYPE: PRT
<213> ORGANISM: Anacardium occidentale

<400> SEQUENCE: 5

Phe His Gly Cys Leu Ala Ser Arg Gln Glu Trp Gln Gln Gln Asp
1               5                   10                  15

<210> SEQ ID NO 6
<211> LENGTH: 15
<212> TYPE: PRT
<213> ORGANISM: Anacardium occidentale

<400> SEQUENCE: 6

Ser Arg Gln Glu Trp Gln Gln Gln Asp Glu Cys Gln Ile Asp Arg
1               5                   10                  15

<210> SEQ ID NO 7
<211> LENGTH: 15
<212> TYPE: PRT
<213> ORGANISM: Anacardium occidentale
```

-continued

```
<400> SEQUENCE: 7

Gln Glu Trp Gln Gln Asp Glu Cys Gln Ile Asp Arg Leu Asp
1               5                   10                  15

<210> SEQ ID NO 8
<211> LENGTH: 15
<212> TYPE: PRT
<213> ORGANISM: Anacardium occidentale

<400> SEQUENCE: 8

Gln Gly Glu Gly Met Thr Gly Ile Ser Tyr Pro Gly Cys Pro Glu
1               5                   10                  15

<210> SEQ ID NO 9
<211> LENGTH: 15
<212> TYPE: PRT
<213> ORGANISM: Anacardium occidentale

<400> SEQUENCE: 9

Tyr Gln Ala Pro Gln Gln Gly Arg Gln Gln Gly Gln Ser Gly Arg
1               5                   10                  15

<210> SEQ ID NO 10
<211> LENGTH: 15
<212> TYPE: PRT
<213> ORGANISM: Anacardium occidentale

<400> SEQUENCE: 10

Gln Gln Gly Gln Ser Gly Arg Phe Gln Asp Arg His Gln Lys Ile
1               5                   10                  15

<210> SEQ ID NO 11
<211> LENGTH: 15
<212> TYPE: PRT
<213> ORGANISM: Anacardium occidentale

<400> SEQUENCE: 11

Gln Asp Arg His Gln Lys Ile Arg Arg Phe Arg Arg Gly Asp Ile
1               5                   10                  15

<210> SEQ ID NO 12
<211> LENGTH: 15
<212> TYPE: PRT
<213> ORGANISM: Anacardium occidentale

<400> SEQUENCE: 12

Ala Ile Pro Ala Gly Val Ala His Trp Cys Tyr Asn Glu Gly Asn
1               5                   10                  15

<210> SEQ ID NO 13
<211> LENGTH: 15
<212> TYPE: PRT
<213> ORGANISM: Anacardium occidentale

<400> SEQUENCE: 13

Leu Asp Arg Thr Pro Arg Lys Phe His Leu Ala Gly Asn Pro Lys
1               5                   10                  15

<210> SEQ ID NO 14
<211> LENGTH: 15
<212> TYPE: PRT
<213> ORGANISM: Anacardium occidentale
```

<400> SEQUENCE: 14

Val Phe Gln Gln Gln Gln Gln His Gln Ser Arg Gly Arg Asn Leu
1               5                   10                  15

<210> SEQ ID NO 15
<211> LENGTH: 15
<212> TYPE: PRT
<213> ORGANISM: Anacardium occidentale

<400> SEQUENCE: 15

Arg Leu Ile Lys Gln Leu Lys Ser Glu Asp Asn Arg Gly Gly Ile
1               5                   10                  15

<210> SEQ ID NO 16
<211> LENGTH: 15
<212> TYPE: PRT
<213> ORGANISM: Anacardium occidentale

<400> SEQUENCE: 16

Lys Val Lys Asp Asp Glu Leu Arg Val Ile Arg Pro Ser Arg Ser
1               5                   10                  15

<210> SEQ ID NO 17
<211> LENGTH: 15
<212> TYPE: PRT
<213> ORGANISM: Anacardium occidentale

<400> SEQUENCE: 17

Val Ile Arg Pro Ser Arg Ser Gln Ser Glu Arg Gly Ser Glu Ser
1               5                   10                  15

<210> SEQ ID NO 18
<211> LENGTH: 15
<212> TYPE: PRT
<213> ORGANISM: Anacardium occidentale

<400> SEQUENCE: 18

Glu Glu Ser Glu Asp Glu Lys Arg Arg Trp Gly Gln Arg Asp Asn
1               5                   10                  15

<210> SEQ ID NO 19
<211> LENGTH: 15
<212> TYPE: PRT
<213> ORGANISM: Anacardium occidentale

<400> SEQUENCE: 19

Leu Lys Trp Leu Gln Leu Ser Val Glu Lys Gly Val Leu Tyr Lys
1               5                   10                  15

<210> SEQ ID NO 20
<211> LENGTH: 15
<212> TYPE: PRT
<213> ORGANISM: Anacardium occidentale

<400> SEQUENCE: 20

Ala Leu Val Leu Pro His Trp Asn Leu Asn Ser His Ser Ile Ile
1               5                   10                  15

<210> SEQ ID NO 21
<211> LENGTH: 15
<212> TYPE: PRT
<213> ORGANISM: Anacardium occidentale

```
<400> SEQUENCE: 21

Leu Asn Ser His Ser Ile Ile Tyr Gly Cys Lys Gly Lys Gly Gln
1               5                   10                  15

<210> SEQ ID NO 22
<211> LENGTH: 15
<212> TYPE: PRT
<213> ORGANISM: Anacardium occidentale

<400> SEQUENCE: 22

Gln Asn Phe Ala Val Val Lys Arg Ala Arg Glu Glu Arg Phe Glu
1               5                   10                  15

<210> SEQ ID NO 23
<211> LENGTH: 15
<212> TYPE: PRT
<213> ORGANISM: Anacardium occidentale

<400> SEQUENCE: 23

Ala Arg Glu Glu Arg Phe Glu Trp Ile Ser Phe Lys Thr Asn Asp
1               5                   10                  15

<210> SEQ ID NO 24
<211> LENGTH: 15
<212> TYPE: PRT
<213> ORGANISM: Anacardium occidentale

<400> SEQUENCE: 24

Pro Glu Glu Val Leu Ala Asn Ala Phe Gln Ile Ser Arg Glu Asp
1               5                   10                  15

<210> SEQ ID NO 25
<211> LENGTH: 15
<212> TYPE: PRT
<213> ORGANISM: Anacardium occidentale

<400> SEQUENCE: 25

Phe Gln Ile Ser Arg Glu Asp Ala Arg Lys Ile Lys Phe Asn Asn
1               5                   10                  15

<210> SEQ ID NO 26
<211> LENGTH: 28
<212> TYPE: DNA
<213> ORGANISM: Escherichia coli

<400> SEQUENCE: 26
tctagagtcg accgccagga atggcaac                                          28

<210> SEQ ID NO 27
<211> LENGTH: 31
<212> TYPE: DNA
<213> ORGANISM: Escherichia coli

<400> SEQUENCE: 27
gcttgcctgc agttaagcat catccctcat g                                      31
```

NUCLEIC ACID AND ALLERGENIC POLYPEPTIDES ENCODED THEREBY IN CASHEW NUTS

RELATED APPLICATION

This application is a division of U.S. application Ser. No. 10/529,602 which was filed on Mar. 30, 2005, now U.S. Pat. No. 7,537,914, and which claimed priority from international application No. PCT/US2003/034960, filed on Apr. 11, 2003, and which claimed priority to U.S. provisional application Ser. No. 60/423,556, filed on Nov. 4, 2002.

FIELD OF THE INVENTION

The present invention relates generally to the field of cell biology and, more particularly, to a nucleic acid sequence and the polypeptides encoded thereby which contain an allergen found in cashew nuts.

BACKGROUND OF THE INVENTION

Allergic reactions to cashew nuts (*Anacardium occidentale*), though relatively infrequent, can be varied and even life threatening reactions include contact or systemic dermatitis (to cardol and anacardic acid found in the cashew nut shell oil) (Marks et al. 1984), atopic dermatitis, and IgE-mediated systemic allergic reactions. (Burks et al. 1998; Tariq et al. 1996; Garcia et al. 2000) Pistachios and mangos are other edible members of the Anacardiaceae family and are allergenic with pistachio showing extensive in vitro and possible clinical cross-reactivity with cashews. (Fernandez, Fiandor, Martinez-Garate, and Martinez 1995) (Parra et al. 1993) (Quercia, Rafanelli, Marsigli, Foschi, and Stefanini 1999). Cashew nuts are widely used in snack foods and as an ingredient in a variety of processed foods such as "butters", bakery and confectionery products.

We have recently demonstrated that the major IgE-reactive proteins in extracts of cashew nut are legumin-like proteins and 2S albumins as assessed by N-terminal and enzymatic fragment sequencing of native proteins. (Teuber, Sathe, Peterson, and Roux 2002) We have also constructed a cashew nut cDNA library and, upon initial screening, cloned and sequenced an allergen in the 7S superfamily, which includes vicilin-like and sucrose binding proteins. (Wang et al. 2002) Here, we present the sequence and characteristics of a second cDNA encoding protein, designated Ana o 2, which is a member of the legumin (11S globulin) family of seed storage proteins. We also describe its reaction with sera from cashew-allergic patients and map its linear epitopes.

REFERENCES CITED

1. Bannon, G. A., G. Cockrell, C. Connaughton, C. M. West, R. Helm, J. S. Stanley, N. King, P. Rabjohn, H. A. Sampson, and A. W. Burks. 2001. "Engineering, Characterization and in Vitro Efficacy of the Major Peanut Allergens for Use in Immunotherapy." *Int Arch Allergy Immunol.* 124:70-72.

2. Beardslee, T A, M G Zeece, G Sarath, and J P Markwell. 2000. "Soybean Glycinin G1 Acidic Chain Shares IgE Epitopes With Peanut Allergen Ara h 3." *Int Arch Allergy Immunol* 123:299-307.

3. Beyer, K, G Grishina, L Bardina, A Grishin, and H A Sampson. 2002. "Identification of an 11S Globulin As a Major Hazelnut Food Allergen in Hazelnut-Induced Systemic Reactions." *J Allergy Clin Immunol* 110:517-23.

4. Bhalla, P. L., I. Swoboda, and M. B. Singh. 2001. "Reduction in Allergenicity of Grass Pollen by Genetic Engineering." *Int Arch Allergy Immunol.* 124:51-54.

5. Bredehorst, R and K David. 2001. "What Establishes a Protein As an Allergen?" *Journal of Chromatography B* 756:33-40.

6. Burks, A W, J M James, A Hiegel, G Wilson, J G Wheeler, S M Jones, and N Zuerlein. 1998. "Atopic Dermatitis and Food Hypersensitivity Reactions." *J Pediatr* 132:132-36.

7. Ehrlich P. 1989. "On Immunity With Special Reference to Cell Life." *Cong. of Immunol '89*:178-97.

8. Eigenmann, P A, A W Burks, G A Bannon, and H A Sampson. 1996. "Identification of Unique Peanut and Soy Allergens in Sera Adsorbed With Cross-Reacting Antibodies." *Allergy Clin Immunol* 98:969-78.

9. Fernandez, C., A. Fiandor, A. Matinez-Garate, and Q. J. Martinez. 1995. "Allergy to Pistachio: Cross-Reactivity Between Pistachio Nut and Other Anacardiaceae." *Clin. Exp. Allergy* 25:1254-59.

10. Fujino, K, H Funatsuki, M Inada, Y Shimono, and Y Kikuta. 2001. "Expression, Cloning, and Immunological Analysis of Buckwheat (*Fagopyrum Esculentum Moench*) Seed Storage Proteins." *J. Agric. Food Chem.* 49:1825-29.

11. Garcia, F, I Moneo, B Fernandez, J M Garcia-Menaya, J Blanco, S Juste, and J Gonzalo. 2000. "Allergy to Anacardiaceae: Description of Cashew and Pistachio Nut Allergens." *J Investig Allergol Clin Immunol* 10:173-77.

12. Heiss, S., V. Mahler, R. Steiner, S. Spitzauer, C. Schweiger, D. Kraft, and R. Valenta. 1999. "Component-Resolved Diagnosis (CRD) of Type I Allergy With Recombinant Grass and Tree Pollen Allergens by Skin Testing." *The Journal of Investigative Dermatology* 113:830-837.

13. Helm, R M, G Cockrell, C Connaughton, H A Sampson, G A Bannon, V Beilinson, D Livingstone, N C Nielsen, and A W Burks. 2000a. "A Soybean G2 Glycinin Allergen. 1. Identification and Characterization." *Int Arch Allergy Immunol.* 123:205-12.

14. Helm, R M, G Cockrell, C Connaughton, H A Sampson, G A Bannon, V Beilinson, N C Nielsen, and A W Burks. 2000b. "A Soybean G2 Glycinin Allergen. 2. Epitope Mapping and Three-Dimensional Modeling." *Int Arch Allergy Immunol.* 123:213-19.

15. Herian, A M, S L Taylor, and R K Bush. 1990. "Identification of Soybean Allergens by Immunoblotting With Sera From Soy-Allergic Adults." *Int Arch Allergy Appl Immunol* 92:193-98.

16. Kleber-Janke, T, R Crameri, U Appenzeller, M Schlaak, and W M Becker. 1999. "Selective Cloning of Peanut Allergens, Including Profilin and 2S 1 bumins, by Phage Display Technology." *Int Arch. Allergy Immunol.* 119:265-74.

17. Marks, J G J., T DeMelfi, M A McCarthy, E J Witte, N Castagnoli, W L Epstein, and R C Aber. 1984. "Dermatitis From Cashew Nuts." *J Am Acad Dennatol* 10:627-31.

18. Niederberger, V., P. Stubner, S. Spitzauer, D. Kraft, R. Valenta, K. Ehrenberger, and F. Horak. 2001. "Skin Test Results but Not Serology Reflect Immediate Type Respiratory Sensitivity: A. Study Performed With Recombinant Allergen Molecules." *J Invest Dermatol* 117:1-5.

19. Parra, F. M., M. Cuevas, A. Lezaun, M. D. Alonso, A. M. Beristain, and E. Losada. 1993. "Pistachio Nut Hypersensitivity: Identification of Pistachio Nut Allergens." *Clin. Exp. Allergy* 23:996-1001.

20. Quercia, O, S Rafanelli, L Marsigli, F G Foschi, and G F Stefanini. 1999. "Unexpected Anaphylaxis to Cashew Nut." *Allergy* 54:895-97.

21. Rabjohn, P, E M Helm, J S Stanley, C M West, H A Sampson, A W Burks, and G A Bannon. 1999. "Molecular Cloning and Epitope Analysis of the Peanut Allergen Ara h 3." *J Clin Invest.* 103:535-42.

22. Sicherer, S. H., T. J. Furlong, A. Munoz-Furlong, A. W. Burks, and H. A. Sampson. 2001. "A Voluntary Registry for Peanut and Tree Nut Allergy: Characteristics of the First 5149 Registrants." *J Allergy Clin Immunol* 108:128-32.

23. Sicherer, S H, A Munoz-Furlong, A W Burks, and H A Sampson. 1999. "Prevalence of Peanut and Tree Nut Allergy in the US Determined by a Random Digit Dial Telephone Survey." *J Allergy Clin Immunol.* 103:559-62.

24. Tariq, S M, M Stevens, S Matthews, S Ridout, R Twiselton, and D W Hide. 1996. "Cohort Study of Peanut and Tree Nut Sensitization by Age of 4 Years." *BMJ* 313:514-17.

25. Teuber, S S, S K Sathe, W R Peterson, and K H Roux. 2002. "Characterization of the Soluble Allergenic Proteins of Cashew Nut (*Anacardium Occidentale* L.)." *Journal of Agricutural Food Chemistry.*

26. Valenta R, Vrtala S, Focke-Tejkl M, Bugajska-Schrefter A, Ball T, Twardosz A, Spitzauer S, Gronlund H. and Kraft D. 1999. "Genetically Engineered and Synthetic Allergen Derivatives: Candidates for Vaccination Against Type I Allergy." *Biol. Chem.* 380815-24.

27. Wang, F, S S Teuber, J M Robotham, P Tawde, S K Satthe, and K H Roux. 2002. "Ana o 1, a Cashew (*Anacardium Occidental*) Allergen of the Vicilin Seed Storage Protein Family." *J Allergy Clin Immunol* 110:160-166.

28. Yamada, K, A Urisu, Y Morita, Y Kondo, E Wada, H Komada, M Yamada, Y Inagaki, and S Torii. 1995. "Immediate Hypersensitive Reactions to Buckwheat Ingestion and Cross Allergenicity Between Buckwheat and Rice Antigens in Subjects With High Levels of IgE Antibodies to Buckwheat." *Ann Allergy Asthma Immunol.* 75:56-61.

29. Zeece, M G, T A Beardslee, J J P Markwell, and G Sarath. 1999. "Identification of an IgE-Binding Region in Soybean Acidic Glycinin G1." *Food Agric Immunol.* 11:83-90.

SUMMARY OF THE INVENTION

With the foregoing in mind, the present invention describes a cloned, expressed and characterized a major cashew allergen. A cashew cDNA library was screened with human IgE and rabbit IgG anti-cashew extract antisera, and a reactive non-vicilin clone, sequenced and expressed as a fusion protein in *E. coli*. Immunoblotting was used to screen for reactivity with patient's sera and inhibition of immunoblotting was used to identify the corresponding native peptides in cashew nut extract. The identified allergen was subjected to linear epitope mapping using the SPOTs solid phase synthetic peptide technology.

Sequence analysis showed the selected clone, designated Ana o 2, to be a member of the legumin family (an 11S globulin) of seed storage proteins. By immunoblotting, 13 of 21 (62%) of sera from cashew allergic patients were reactive. Immunoblot inhibition data showed the native Ana o 2 constitutes a major band at ~33 kD and a minor band at ~55 kD. Probing of overlapping synthetic peptides with pooled human cashew-allergic sera identified 22 reactive peptides, 7 of which gave strong signals. Several Ana o 2 epitopes were shown to overlap those of the peanut allergenic legumin, Ara h 3, in position but with little sequence similarity. Greater positional overlap and identity was observed between Ana o 2 and soybean glycinin epitopes. Conclusion: We conclude that this legumin-like protein is a major allergen in cashew nuts.

BRIEF DESCRIPTION OF THE DRAWINGS

Some of the features, advantages, and benefits of the present invention having been stated, others will become apparent as the description proceeds when taken in conjunction with the accompanying drawings in which:

FIG. 1 shows the nucleotide and derived amino acid sequence analysis of Ana o 2 cDNA clone Ana o 2; this figure includes subfigures A1 and 2, B, C, and D, all of which may be collectively referred to as FIG. 1, and wherein FIGS. 1 A1 and 1A2, respectively, show the nucleotides of SEQ ID NO:1, including a stop codon shown underlined and in bold; and the nucleotides of SEQ ID NO:2;

FIG. 1 B shows the derived amino acid sequence of the Ana o 2 coding region (SEQ ID NO:1) shown with the presumed signal sequence underlined, sites of sequence insertions shown in bold text, deletions shown in double underline in the nine most similar sequences in GenBank (see Table I) as compared to Ana o 2 indicated; sequences similar to previously reported cashew legumin group proteins derived by amino acid sequencing, (Teuber 2002) are shown in bold italics;

FIG. 1 C shows details on the sites of insertion (red) and Deletions (blue) as described herein; a vertical line between residues indicates the sites of insertions in similar peptides with the insertion size (number of amino acids) and plant species (two or three letter code) shown above the insertion site; deletions are underlined or overlined, and only deletions and insertions of three or more residues are included; abbreviations used are as follows: Rc, *Ricinus communis*; Cav, *Corylus avellana*; Qr, *Quercus robur*; Ahy, *Amaranthus hypochondriacus*; Si, *Sesamum indicum*; Ms, *Magnolia salicifolia*; Vs, *Vicia sativa*; Cp, *Cucurbita pepo*; Car, *Coffea arabica*; Ah3, *Arachis hypogaea* (Ara h 3); and Ah4, *Arachis hypogaea* (Ara h 4); and FIG. 1 D shows a comparison of cDNA—derived Ana o 2 sequences to similar sequences of previously reported cashew legumin group proteins derived by amino acid sequencing. (Teuber et al. 2002) Identical residues are in bold. Accession number: AF453947;

FIG. 3 shows a comparison of the IgE-binding epitopes of various 11S globulins to those of the cashew legumin, Ana o 2; bracketed and numbered regions indicate locations of the reactive peptides in Ana o 2 (also listed in TABLE III); shaded segments indicate regions expressing one or more linear epitopes on the different allergens; identical amino acids are indicated with a "." while similar residues are depicted with a "|"; the symbol "/" shows where a portion of a sequence was deleted and a "-" represents where a space was added in the sequence to maximize alignment; the presumed cleavage site between the acidic and basic subunits (between amino acids 271 and 272) is shown in text above the sequence; boxes denote regions where numerous insertions and deletions are found when comparing multiple legumin sequences (see FIG. 1C).

DETAILED DESCRIPTION OF THE PREFERRED EMBODIMENT

Figure 2:
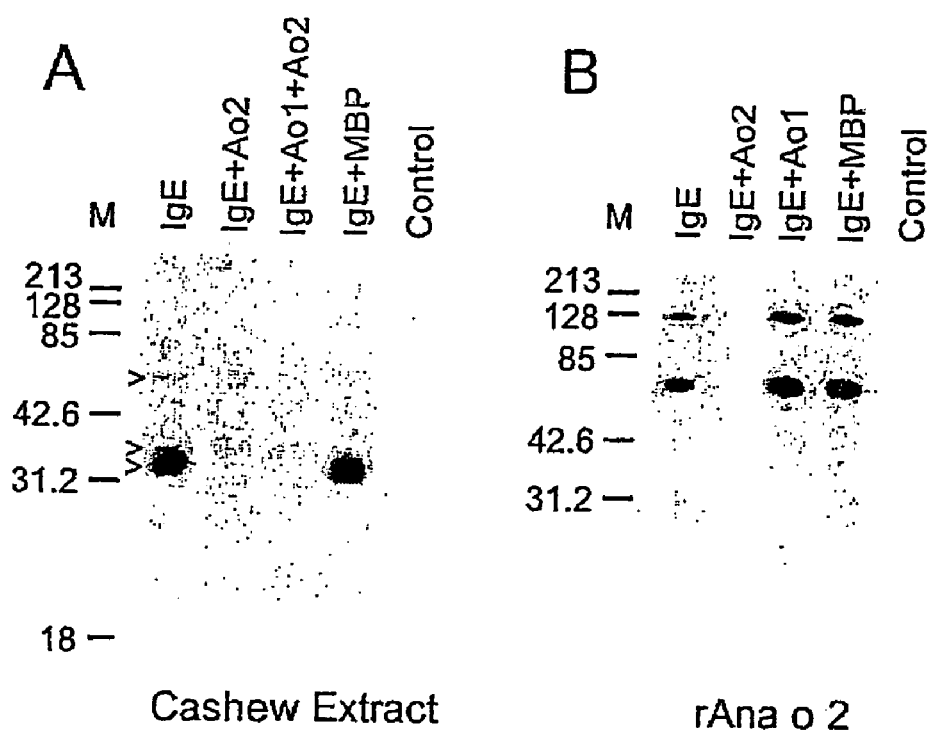
FIG. 2 shows the identification of native Ana o 2 peptide in cashew extract by means of Western blotting, wherein nitrocellulose blots of total cashew extract (A) and rAna o 2 (B) were probed with serum from cashew-allergic patient (#9) and tagged with 125I-labeled anti human IgE; the first (left) lane in each blot was incubated without inhibition; the second through fourth lanes were incubated with rAna o 2, rAna o 1 and/or MBP as indicated; the right lanes were incubated with control human sera; arrows indicate locations of native Ana o 1, top, Ana o 2 (acidic subunit), bottom, and an, as yet, unidentified band, middle; the lower and upper bands in (B) representing the uncleaved (precursor) form of rAna o 2 in its monomer and presumptive dimer configurations, respectively.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Moreover, these illustrated embodiments are provided so that this disclosure will be thorough and complete, and will fully convey the scope of the invention to those skilled in the art. Other features and advantages of the invention will be apparent from the following detailed description, and from the claims.

Abbreviations Used

Amino acids: the standard one-letter abbreviations are used.

DTT: dithiothreitol.

HRP; horseradish peroxidase.

Nucleotides: the standard one-letter abbreviations are used.

PCR: polymerase chain reaction.

PBS: phosphate buffered saline.

DS-PAGE: sodium dodecyl sulfate polyacrylamide gel electrophoresis.

TBS: tris-buffered saline.

Methods

Human Sera

Blood samples were drawn after informed consent from patients with life-threatening systemic reactions to cashew nut and the sera frozen at −70° C. until use. The study was approved by the human subjects review committee of the University of California at Davis. The presence of cashew-reactive IgE was confirmed by Pharmacia ImmunoCAP assay (Pharmacia, Uppsala, Sweden) or by Western immunoblotting. Control sera were obtained from patients with a history of anaphylaxis to walnut, pistachio or hazelnut who reported tolerance of cashews.

Cashew Protein Extract

An albumin/globulin extract was prepared as previously described. Protein concentrations were measured by use of the Bradford protein assay (BioRad Laboratories, Inc., Hercules, Calif.) using bovine serum albumin as the standard protein.

Production of Rabbit Polyclonal Antiserum

A rabbit was immunized with 5 mg of cashew extract in Freund's complete adjuvant and boosted four weeks later with 5 mg of cashew extract in incomplete Freund's adjuvant. The rabbit was subsequently bled and the serum stored at −20° C. Guidelines for animal care and welfare as in the "Guide for the Care and Use of Laboratory Animals" prepared by the Institute of Laboratory Animal resources, National Research Council, National Academy Press, revised 1996, were followed.

Construction and IgE Immunoscreening of Cashew cDNA Library

Library construction and immunoscreening have previously been described in detail. (Wang 2002) Briefly, cashew nuts in late maturation were chopped, frozen, and ground. Total RNA was extracted in TRIzol (GIBCO BRL Life Technologies Inc., Rockville, Md.) and mRNA was isolated using a PolyATtract kit (Promega, Madison, Wis.). The cDNA library was constructed using the Uni-ZAP XR Gigapack Cloning Kit (Stratagene Inc., Cedar Creek, Tex.) and cloned into the lambda Uni-ZAP XR expression vector. The library was amplified in E. coli strain XL1-Blue and screened with rabbit (IgG) and human (IgE) antisera. The immunopositive clones were picked, plaque-purified, and stored in SM buffer supplemented with 2% chloroform at 4° C.

Sequencing and Corresponding Analysis of Selected Genes

Inserts from the selected phage clones were amplified with M13 forward and reverse primers by PCR. Both strands of the PCR products were then sequenced on an ABI 3100 Genetic Analyzer (Foster City, Calif.) using capillary electrophoresis and Version 2 Big Dye Terminators as described by the manufacturer. Similarity searches and alignments of deduced amino acid sequences were performed on Genetics Computer Group (GCG) software (Accelrys, Inc. San Diego, Calif.) using the BLAST 2.0 program (www.ncbi.nim.nih.gov/BLAST/).

Cloning, expression and purification of cDNA-encoded proteins.

As previously described in detail (Wang et al. 2002), cDNA coding sequences were modified by the addition of a Sal I site at 5' end and a Pst I site at 3'end by PCR using PfuTurbo DNA polymerase (Stratagene Inc., Cedar Creek, Tex.) followed by digestion with Sal I and Pst I and ligation to maltose binding protein (MBP) fusion expression vector pMAL-c2 (New England BioLabs Inc., Beverly, Mass.), into which a thrombin cleavage site had been engineered.

For expression, competent E. coli BL21 (DE3) cells (Novagen Inc., Madison, Wis.) were transformed. Positive clones were identified by PCR screening using cDNA sequence-specific primers. Single colonies were grown and induced with isopropyl-D-thiogalactopyranoside (IPTG). The cells were harvested, lysed with mild sonication, and centrifuged at 12,000 g. The lysate supernatant was passed over an amylose affinity column and the fusion protein eluted with 10 mM maltose. The cDNA insert was produced by PCR amplification of the portion of the sequence extending from the presumed first codon following the leader peptide through the last codon prior the stop codon using the primers TCTAGAGTCGACCGCCAGGAATGGCAAC (forward) and GCTTGCCTGCAGTTAAGCATCATCCCTCATG (reverse). Fusion proteins were cleaved with thrombin (Sigma, St. Louis, Mo.) and the liberated recombinant protein purified on a Superdex 200 column (Amersham Pharmacia, Piscataway, N.J.) by high performance liquid chromatography (HPLC). Cleaved and un-cleaved recombinant proteins were concentrated and either stored (briefly) at 4° C. until use or frozen at −70° C.

Gel Electrophoresis (SDS-PAGE), Immunoblotting, and Inhibition rAna 0 2 (at 10 g/4 mm width) or total cashew extract (100 g/4 mm width) samples were boiled in reducing sample buffer and subjected to electrophoresis, immunoblotting and inhibition as previously described (Wang et al. 2002). For inhibition experiments, 10 g of rAna o 2, rAna o 1, and/or MBP were pre-incubated with human antiserum (from patient #9 at 1:20 dilution) for 1 hr at 37° C. and then incubated with nitrocellulose strips containing blotted cashew extract overnight at 4° C. The strips were then incubated with the appropriate labeled second antibody and exposed to x-ray film.

Solid-Phase Peptide (SPOTs) Synthesis and Binding to IgE

Based on the derived amino acid sequence of the 457 amino acid Ana o 2 protein (including the presumptive leader sequence, amino acids 1-14), 57 overlapping 15-amino acid peptides, each offset by eight amino acids, were synthesized. An additional peptide, corresponding to presumptive N-terminal amino acid, 15-29, was also produced. Peptides were synthesized on derivatized cellulose sheets using 9-fluorenlymethoxy carbonyl-derived (Fmoc) amino acids (Genosys Biotechnologies, Inc., The Woodlands, Tex.) and probed as previously described (Wang et al. 2002). Briefly, the peptide-containing membranes were washed in TBS and incubated o/n at RT in blocking solution, washed in TBS-T and incubated o/n at 4° C. with pooled patients' sera diluted 1:5 (v:v). This incubation was followed by three 5-min washes in TBS-T and an o/n (4° C.) incubation with 125I-anti-human IgE (Hycor Biomedical Inc.) diluted 1:10 in a mixture of PBS, 5% nonfat dry milk, and 0.05% Tween-20. After additional washes, IgE-peptide reactivity was identified after a 1-week exposure at −70° C. to x-ray film or a 17 hr incubation with a Molecular Dynamics phosphoimaging screen (Kodak). Phosphoimaging data was quantified using a Storm 860 scanner (Molecular Dynamics) and its accompanying software.

Results cDNA Library Screening and Gene Characterization

The cDNA library was initially screened for reactivity with both rabbit IgG and (cashew-allergic) human IgE. As previously reported, a total of 50 clones displaying dual reactivity were selected for further analysis (Wang et al. 2002). The first four clones selected for sequencing all proved to encode one of two vicilin variants and were designated Ana o 1.1 and Ana o 1.2. A further analysis of the remaining 46 clones by PCR using Ana o 1 specific primers showed that 45 of the 46 were Ana o 1-positive. The remaining clone, upon sequencing and comparison to GenBank, proved to be homologous with the legumin family of seed storage proteins (FIG. 1A) and was designated, Ana o 2. Table I lists the nine proteins having the highest degrees of identity (45% to 58%) and similarity (63% to 74%) to Ana o 2 and include proteins described as legumin-like, legumin precursor, legumin A precursor, 11S globulin, and 11S globulin b-subunit precursor, representing a diversity of tree and plant species (Table I). Also listed are four 11S family proteins with somewhat lower identity (42%-47%) and similarity (58%-66%) but which have previously been identified as legumin allergens. Two of the allergens are from the peanut, Ara h 3 and Ara h 4, and two from soybean, the glycinin G1 and G2 subunits.

Protein Sequence Characterization.

Analysis of the nucleotide (FIG. 1A) and deduced amino acid sequences (FIG. 1B) reveal a 457 amino acid open reading frame, a possible start site at position 93, and possible leader peptide from 1 to 15. Comparison of the nine most similar sequences and the four above mentioned allergens (listed in Table I) with Ana o 2 amino acid sequence shows clustered sites of insertions (red segments) and deletions (blue segments). FIG. 1C shows the sites of insertions (blue over and underlined) and deletions (red vertical lines) of four or more amino acids in the eleven compared sequences with respect to the Ana o 1 sequence. Multiple insertions are seen between amino acid 14 and 23, 104 and 121, and 180 and 198 with additional scattered insertions between 247 and 271. In contrast to the 24 insertion, only four deletions are present, all of which are clustered in the 245 to 270 region.

We have previously reported N-terminal and tryptic peptide sequences for several native IgE reactive cashew proteins (Teuber et al. 2002). Four of these were found to have similarity to the cDNA sequence of Ana o 2 (FIG. 1D and green sequence segments in FIG. 1B) though none was identical suggesting that Ana o 2 is a member of a larger gene family or that there is extensive polymorphism at the relevant loci.

Reactivity of the recombinant protein with human IgE and rabbit IgG.

For immunological characterization, we cloned and expressed Ana o 2 beginning at nucleotide 47 (after the presumptive leader peptide) through 1375. The DNA segment was ligated into an expression vector designed to allow for purification of the recombinant molecule via a mannose-binding protein (MBP) fusion domain in conjunction with an amylose affinity column and a thrombin-specific cleavage site. The resulting ~93 kD Ana o 2 fusion protein was affinity purified as previously described and digested with thrombin to yield a ~52 kD peptide as well as the 43 kD MBP (data not shown). Both cleaved and uncleaved peptides were reactive with specific human IgE and rabbit IgG (data not shown).

Recognition of Ana o 2 as an Allergen

The prevalence of reactivity to rAna o 2 among cashew allergic patients by Western immunoblotting is shown in Table 2. IgE from 13 of 21 (62%) sera from patients with a history of life-threatening reactions to cashews bound the recombinant. In 6 cases, the intensity of the signal was strong, but was weak in 7 cases. In contrast, 1 of 10 sera from patients tolerant of cashew but clinically with life-threatening reactions to other tree nuts reacted with the rAna o 2.

Identification of Native Ana o 2 by SDS-PAGE Immunoblotting.

Having established that Ana o 2 is a major cashew allergen, we next sought to identify the band or bands in a typical total cashew immunoblot that correspond to the cloned polypeptide storage protein precursor. FIG. 2A shows nitrocellulose strips in which the total soluble cashew extract has been blotted and probed with serum from an allergic patient #9. The first strip (left lane) shows this serum reacting with three major bands at ~55, ~36 and ~33 kD. The second through fourth lanes were incubated with the same human sera preincubated with rAna o 2, rAna o 1+rAna o 2, and the fusion protein, MBP, respectively. Note that Ana o 2 inhibits the strong band at ~33 kD and weakens the band at ~55 kD. The addition of Ana o 1 inhibits the residual signal at ~55 kD. MBP has no inhibitory effect as expected. The remaining band at ~36 kD is as yet unidentified. The last lane (right) shows no reactivity with a patient having allergies to agents other than cashew.

FIG. 2B shows reactivity of the human sera with rAna o 2 (~53 kD) and its inhibition with purified rAna o 2 but not rAna o 1 nor MBP. The band at ~120 kD is presumed to be a dimer of rAna o 2.

Identification and Recognition of IgE-reactive Linear Epitopes on Ana o 2 and Comparison to Peanut and Soybean Legumin Epitopes.

The entire amino acid length of Ana o 2 was studied by probing 58 overlapping solid phase synthetic peptides with sera from 12 patients randomly assigned to three pools. Collectively, the three pools reacted weakly (phosphoimaging score from 2.0-3.9×10-3) with 12, moderately (4.0-6.9×10-3)

with three, and strongly (7.0×10-3) with seven linear IgE-binding epitopes. The 22 reactive epitopes were distributed throughout the length of the protein (Table III) with 68% (15/22) of all epitopes residing on the presumed acidic chain of the protein, including 86% (6/7) of those epitopes that were found to react strongly with pooled patient IgE. Only two of the identified epitopes were bound by patients' sera from all three pools. Epitope #6 was bound strongly by pools 1 and 3, and moderately by pool 2. Epitope #3 was bound strongly by pool 1, but moderately by pools 2 and 3.

To compare the linear epitopes of cashew legumin (Ana o 2) to those of peanut (Ara h 3) (Rabjohn et al. 1999) and the soybean legumins (G2 and G1 glycinin) (Helm et al. 2000b) (Beardslee et al. 2000), we aligned the sequences using the BLAST 2.0 program and highlighted the corresponding linear epitopes (FIG. 3). Of the regions included in the BLAST alignment, only two of the 22 Ana o 2 linear epitope-bearing peptides (#13 and 15) showed significant (>7 amino acid) positional overlap with any of the four previously identified peanut Ara h 3 epitope-bearing peptides (FIG. 3) (Rabjohn et al. 1999). Even among these two overlapping epitope regions, there was little identity or similarity between the Ana o 2 and Ara h 3 (Rabjohn et al. 1999). A much greater degree of correspondence was observed when the sequences of Ana o 2 and G2 glycinin were aligned; 9 of the 11 (89%) previously identified G2 glycinin epitopes showed significant positional overlap with the Ana o 2 epitopes. All 9 showed a significant degree of similarity (60%) and two were quite similar in sequence to Ana o 2 epitopes #1 (77%) and the adjacent pair, #10 and #11 (80%) (FIG. 3). Two IgE-binding linear epitopes have been identified on G1 glycinin (Beardslee et al. 2000), both on the acidic chain. Sequence alignment revealed that only the second glycinin epitope displayed significant positional overlap and no significant identity with a cashew legumin epitope (#13). Interestingly, this epitope (#13) is the only one identified that displays positional overlap with an epitope in each of the other three compared 11S globulins (FIG. 3) suggesting the possibility of a shared structural motif favoring immunogenicity.

Comparison of rAna o 2 to Native Peptides

We have recently reported the N-terminal and tryptic peptide sequences of four legumin proteins bands (Teuber et al. 2002). In comparing these sequences to those of rAna o 2, we note that none are identical in sequence (Table IV). One tryptic peptide matched at 8 of 9 positions. Two other nearly identical tryptic peptides matched rAna o 2 at only 13 of 19 position and 12 of 18 positions. An N-terminal peptide matched at 7 or 8 of 10 positions beginning at residue 272 of rAna o2. Together, these data suggest that these represent a complex family of differentially processed proteins.

Discussion

Approximately 0.5% of the US population is believed to be allergic to tree nuts (Sicherer et al. 1999) and the data from a voluntary registry of peanut and tree nut allergic US patients shows 20% of those reporting allergy to tree nuts list sensitivity to cashews, the highest percentage for any tree nut. (Sicherer et al. 2001). In another study, restricted to pediatric patients (n=54) at Johns Hopkins (Baltimore, Md., USA), cashew reactivity ranked fourth (11%) behind walnut (26%), almond (13%), and, pecan (13%), perhaps reflecting a delayed dietary introduction of cashews relative to other nuts. (Ehrlich P. 1989)

A number of plant, animal and fungal allergenic proteins have been identified by biochemical and molecular genetic means in recent years reflecting the hope that the detailed information provided by such studies will lead to the development of hypoallergenic foods, new therapeutic and diagnostic tools, and an increased understanding of the properties that render some proteins more allergenic than others.(Heiss et al. 1999; Valenta R et al. 1999; Bannon et al. 2001; Niederberger et al. 2001; Bhalla et al. 2001)

Our previous screening of a cashew nut cDNA library with human cashew-allergic sera primarily yielded clones encoding an IgE-reactive vicilin-like protein, designated Ana o1 (Wang et al. 2002). Here we describe the product of the single identified clone encoding a legumin-family (11S globulin) seed storage protein, designated Ana o 2.

The legumins are large (300-450 kD), generally hexameric, non-glycosylated members of a complex family of proteins. Individual subunits are found both as intact precursor proteins (50-60 kD) and as processed acidic (30-40 kD) and basic (20 kD) subunits that generally remain covalently associated in seeds. In addition to Ana o 2, several other legumins have been identified as food allergens. These include Ara h 3 (Rabjohn et al. 1999) and Ara h 4 (Kleber-Janke et al. 1999) of the peanut, the soybean G1 and G2 glycinins (Zeece et al. 1999; Helm et al. 2000a; Beardslee et al. 2000), Cor a 9 of the hazelnut (Beyer et al. 2002), and possibly a legumin from buckwheat (Fujino et al. 2001; Yamada et al. 1995). The legumins are related to each other structurally and are believed to share ancestors in common with vicilin-like 7S proteins. The vicilins, or 7S globulins, are also multimeric, digestion resistant, seed storage molecules found in many edible plants and are frequently allergenic.

More than 50% of the sera from cashew allergic patients (13 of 21, 62%) reacted with rAna o 2 formally making this a major allergen. Six of the sera reacted strongly (29%). Because of the known complexity of the legumin family, and the differences observed between the single recombinant cashew legumin cDNA-derived sequence reported here and the sequenced cashew peptide fragments from IgE-reactive proteins previous reported (Teuber et al. 2002) it would not be unexpected if additional reactivity to legumin epitopes not represented on our cloned and expressed version were yet to be discovered. Nevertheless, at least for the patient's serum tested, it appears that the recombinant protein fully inhibited reactivity to the native extracted protein suggesting that most or all members of the cashew legumin family share common allergenic epitopes. However, further investigations comparing additional cloned versions the legum ins to each other and to highly purified native molecules for reactivity to human IgE will be needed to adequately determine if this Ana o 2 clone expresses the full range of cashew legumin allergenic epitopes. The unique IgE-binding patterns of each pool of sera to the Ana o 2 linear epitopes suggests a heterogeneity of recognition patterns between patients though some peptides were recognized by members of two or all three pools.

Linear epitope mapping has shown that the soybean G1 glycinin acidic chain may share cross-reactive epitopes with the peanut Ara h 3 (Beardslee et al. 2000). Both epitopes mapped from the G1 acidic chain show a considerable degree of identity (60% and 70%) with the overlapping region of the homologous Ara h 3 epitopes though differences were noted in the critical amino acids.(Beardslee et al. 2000) It has been shown directly that the IgE-binding regions of the soybean G2 glycinin also bind IgE from peanut sensitive patients [Helm 2000]. Such findings are not surprising when one considers that both are members of the legume family and patients allergic to one have serum IgE antibodies that immunologically cross-react with other legumes. (Eigenmann et al. 1996). While no such direct analysis has been performed to determine if there is cross-reactivity between our cashew legumin (Ana o 2) and that of peanut (Ara h 3) and soybean (G1 and G2 glycinin), the BLAST alignment of these protein sequences and subsequent analysis of the positional relationship and degree of homology between linear epitopes on each protein has been informative. The major findings are that there is considerable positional overlap and some shared sequence identify between Ana o 2 and soybean G2 glycinin but little in common between Ana o 2 and peanut Ara h 3 linear epitopes. We have shown that the majority of Ana o 2 linear epitopes (68% overall and 83% of the most strongly reactive) are on the acidic chain of the protein. Previous studies have also observed stronger reactivity with the acidic chain rather than the basic chain of allergenic legumins [Pederson 1989](Herian et al. 1990; Rabjohn et al. 1999; Beardslee et al. 2000)[Helm 2000].

It is worth noting that the majority of Ana o 2 epitopes are located in the same areas of the protein sequence that is evolutionarily least conserved with respect to insertions and deletions among a variety of legumins (compare FIG. 2C with the acidic chain of Ana o 2 in FIG. 3); features that would further minimize cross-reactivity between plant legumins. It should also be borne in mind though that these various results represent only those reactions between a subset of legumin sequences in each of the compared plant seeds and the IgE from a limited set of patients. The inclusion of additional legumins and a broader pool of patient sera in future analyses could shed further light on these various relationships.

Clinical information regarding cross-reactivity between cashews and legumes has not been well documented, but based on our findings we can predict that while there may be a basis for cross-reactivity between cashew and soybean, it is unlikely that such cross-reactivity exists between cashew and peanut legumins, at least with regard to linear epitopes. Similarly, we previously reported that cross-reactivity between the vicilin linear epitopes of cashew (Ana o 1) and peanut (Ara h 1) would also be unlikely (Wang et al. 2002), observations which, together, further explains the lack of cross-reactivity between tree nut- and peanut-reactive patients' sera (Sicherer et al. 2001).

To date, no common structural characteristics of linear-IgE epitopes have been identified (reviewed in (Bredehorst and David 2001)), but our finding that all four legumins analyzed share an epitope with positional overlap, suggests that epitope mapping can provide important clues to the nature of allergenicity. Three-dimensional modeling of our cashew legumin is continuing and when compared to the models of G2 glycinin (Helm et al. 2000b) and other homologous allergens, may provide additional insights.

The Various Aspects of the Claimed Invention

The present invention thus discloses isolated nucleic acid sequences, polypeptide products thereof, and associated methods. The skilled will recognize that the isolated nucleic acids will be useful at least when expressed in a suitable cell or organism to produce the encoded polypeptides, which in turn may be employed in testing to identify patients allergic to cashew nuts. Furthermore, expression of the nucleic acid sequences of the present invention in a suitable cell may be useful in studying and characterizing gene function.

Accordingly, the present invention includes an isolated nucleic acid sequence comprising the nucleotide sequence of SEQ ID NO:1, or a degenerate variant of SEQ ID NO:1. SEQ ID NO:1 is the coding sequence for the described Ana-o-2 cashew antigen, including a stop codon "TAA" at positions 1372-1374. The nucleic acid sequence described may also comprise at least one mutation selected from a deletion, a substitution, and an addition. A preferred embodiment of the invention includes an expression vector comprising the nucleic acid sequence noted above operably linked to an expression control sequence, and a cultured cell comprising this vector, the cell, or a progeny of the cell, preferably being transfected with the vector, wherein the cell expresses a polypeptide encoded by said nucleic acid sequence. The nucleic acid of SEQ ID NO:1 may also further comprise additional nucleotides according to SEQ ID NO:2, which provides a tail for the coding sequence. Additionally, the invention further includes an isolated nucleic acid comprising a sequence that encodes a polypeptide comprising the amino acid sequence of SEQ ID NO:3. An additional aspect of the invention includes a method of producing a protein by culturing the cell containing nucleic acid sequence SEQ ID NO:1 under conditions permitting expression of a polypeptide encoded by the nucleic acid. The method may also include purifying the polypeptide from the cell or the medium of the cell.

The invention also discloses twenty-two (22) linear polypeptide epitopes, as listed in Table III, which are also respectively listed herein as SEQ ID NO:4 through SEQ ID NO:25. Accordingly, the invention includes an isolated nucleic acid comprising a sequence that encodes a polypeptide comprising an amino acid sequence selected from SEQ ID NOS:4-25. Additionally claimed is a purified Ig-E binding polypeptide the amino acid sequence of which comprises at least one sequence selected from SEQ ID NOS:4-25, and wherein the polypeptide comprises at least one mutation in said selected amino acid sequence, the mutation being selected from a deletion, a substitution, an addition, and particularly a mutation which reduces the polypeptide's IgE-binding capacity but retains at least some immunogenicity. Those skilled in the art should recognize that the scope of the invention includes an isolated nucleic acid sequence or a degenerate variant thereof, which encodes a polypeptide consisting essentially of an amino acid sequence selected from SEQ ID NOS:4-25, and that the selected amino acid sequence may include at least one mutation such as a deletion, a substitution, or an addition. It should be understood that by "essentially" it is meant that the polypeptide is largely, but not wholly, the specified sequence.

Further method aspects of the disclosed invention include a test for detecting a cashew allergy in a patient, said test comprising contacting the patient with an amount of a purified polypeptide comprising at least one amino acid sequence selected from SEQ ID NOS:3-15. In this test, contacting preferably comprises introducing the purified polypeptide into the patient, for example, by injection. The skilled will know that injecting includes any of the known routes useful in immunological testing of patients, for example, intradermally, and subcutaneously. Additionally, the purified polypeptide for use in such a test may comprise at least one mutation in said amino acid sequence, and the mutation may be selected from a deletion, a substitution, and an addition.

Yet a further diagnostic test of the invention for detecting anti-cashew IgE in a patient to thereby indicate an allergy to cashews, the test comprising several steps. The patient's serum is reacted with a purified polypeptide the amino acid sequence of which comprises at least one sequence selected from SEQ ID NOS:4-25. The polypeptide is separated from unreacted patient serum, and the polypeptide is reacted with a labeled human IgE-reactive agent after separating from unreacted patient serum. The polypeptide is then separated from unreacted labeled human IgE-reactive agent, and the labeled human IgE-reactive agent bound to the polypeptide after separating from unreacted agent is detected directly or indirectly to thereby indicate presence in the patient's serum of anti-cashew IgE. The amino acid sequence of the polypeptide for use in this test may also comprise at least one mutation selected from a deletion, a substitution, and an addition.

The invention also includes a test for screening patients for allergy to cashews which may be embodied in a test kit comprising a first reagent containing at least one purified polypeptide whose amino acid sequence comprises at least one sequence selected from SEQ ID NOS:4-25. The test kit preferably also includes a second reagent containing at least one labeled human IgE-reactive agent. Additionally, in the test kit the first reagent may include a solid phase carrying the purified polypeptide.

The skilled will find additional guidance in carrying out the invention by consulting Sambrook et al., 1989, Molecular Cloning, A Laboratory Manual, Cold Spring Harbor Press, N.Y., and also Ausubel et al. (eds.), 1995, Current Protocols in Molecular Biology (John Wiley & Sons, N.Y.). In addition, guidance in diagnostic and screening test methods suitable for use with the polypeptides of the present invention may be found in Manual of Clinical Laboratory Immunology, Sixth Edition, Rose et al. (eds.), 2002, American Society for Microbiology, Washington, D.C. As noted above, these publications are incorporated herein in their entirety.

Accordingly, in the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

Sequence Listings

Following is a written sequence listing for nucleic acid SEQ ID NOS: 1-2 and for polypeptides SEQ ID NOS:3-25. Also enclosed is a complete sequence listing in computer readable form. The information recorded on the form is identical to the written sequence listing.

The invention claimed is:

1. A purified IgE binding immunogenic polypeptide wherein the amino acid sequence of which comprises at least one sequence selected from the group consisting of SEQ ID NOS:4-25.

2. A test kit for screening patients for allergy to cashews, said kit comprising a first reagent containing at least one purified polypeptide whose amino acid sequence comprises at least one sequence selected from the group consisting of SEQ ID NOS:3-25.

3. The test kit of claim 2, further comprising a second reagent containing at least one labeled human IgE-reactive agent.

4. The test kit of claim 2, wherein said first reagent further comprises a solid phase carrying the purified polypeptide.

* * * * *